United States Patent
Nosovitskiy et al.

(10) Patent No.: US 10,215,743 B2
(45) Date of Patent: *Feb. 26, 2019

(54) INTRODUCING PERIODICITY FOR DISCRETE DETERMINATION OF CONCENTRATIONS OF GASES IN A GASEOUS MIXTURE

(71) Applicants: Pavel Nosovitskiy, San Francisco, CA (US); Gennadiy Nosovitskiy, Round Lake, IL (US)

(72) Inventors: Pavel Nosovitskiy, San Francisco, CA (US); Gennadiy Nosovitskiy, Round Lake, IL (US)

( * ) Notice: Subject to any disclaimer, the term of this patent is extended or adjusted under 35 U.S.C. 154(b) by 664 days.

This patent is subject to a terminal disclaimer.

(21) Appl. No.: 14/869,912

(22) Filed: Sep. 29, 2015

(65) Prior Publication Data

US 2016/0258920 A1    Sep. 8, 2016

Related U.S. Application Data

(63) Continuation-in-part of application No. 13/471,310, filed on May 14, 2012, now Pat. No. 9,164,073, which is a continuation-in-part of application No. 12/322,989, filed on Feb. 10, 2009, now Pat. No. 8,185,325.

(60) Provisional application No. 61/065,458, filed on Feb. 11, 2008.

(51) Int. Cl.
*A61B 5/08* (2006.01)
*G01N 33/00* (2006.01)
*A61B 5/1468* (2006.01)
*G01N 33/497* (2006.01)

(52) U.S. Cl.
CPC .......... *G01N 33/0062* (2013.01); *A61B 5/082* (2013.01); *G01N 33/0016* (2013.01); *G01N 33/497* (2013.01); *A61B 5/1468* (2013.01); *A61B 2562/02* (2013.01)

(58) Field of Classification Search
None
See application file for complete search history.

(56) References Cited

U.S. PATENT DOCUMENTS

| | | | | |
|---|---|---|---|---|
| 8,185,325 B2 * | 5/2012 | Nosovitskiy | ....... | A61B 5/14532 365/94 |
| 9,164,073 B1 * | 10/2015 | Nosovitskiy | ....... | G01N 33/0031 |

OTHER PUBLICATIONS

Llobet et al. Qualitative and quantitative analysis of volatile organic compounds using transient and steady-state responses of a thick-film tin oxide gas sensor array Sensors and Actuators B vol. 41, pp. 13-21 (Year: 1997).*

Yu et al. Analysis of diabetic patients breath with conducting polymer sensor array Sensors and Actuators B vol. 108, pp. 305-308 (Year: 2005).*

* cited by examiner

*Primary Examiner* — John S Brusca

(57) ABSTRACT

Methods, system and device are provided for detection and quantitative and qualitative analysis of components in a gaseous mixture distinguished by high selectivity and high resolution. The influence of individual gases may be distinguished through detection of changes associated with a sensor's sensitive layer that interacts with the components of the gaseous mixture. Through periodic variations of parameters or conditions of the sensor, the characteristics of the gas components may be derived. For example, the concentration of a gas or multiple gases in a mixture may be determined with a high degree of accuracy. Non-invasive detection of biological off-gases may be implemented. Other uses abound.

18 Claims, 6 Drawing Sheets

INTRODUCING PERIODICITY FOR DISCRETE DETERMINATION OF CONCENTRATIONS OF GASES IN A GASEOUS MIXTURE

CROSS-REFERENCE TO RELATED APPLICATIONS

For purposes of the USPTO extra-statutory requirements, the present application constitutes a continuation-in-part of U.S. patent application Ser. No. 12/322,989 filed 10 Feb. 2009, which is currently co-pending, or is an application of which a currently co-pending application is entitled to the benefit of the filing date. Said '989 application claims priority to a U.S. provisional application Ser. No. 61/065,458 which was filed 11 Feb. 2008. The present application also constitutes a continuation-in-part of U.S. patent application Ser. No. 13/471,310 filed on 14 May 2012.

The United States Patent Office (USPTO) has published a notice to the effect that the USPTO's computer programs require that patent applicants reference both a serial number and indicate whether an application is a continuation or continuation-in-part. Stephen G. Kunin, Benefit of Prior-Filed Application, USPTO Official Gazette 18 Mar. 2003. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications.

Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s). All subject matter of the Related Applications and of any and all parent, grandparent, great-grandparent, provisional, etc. applications of the Related Applications is incorporated herein by reference to the extent such subject matter is not inconsistent herewith. Where there is determined to be a conflict, the subject matter and description described herein controls.

BACKGROUND

Field of the Invention

The disclosure relates to measuring and testing, particularly for gas analysis, for example breath analysis of organisms and subclasses of breath analysis inside the body. The disclosure most closely relates to technical fields including chemistry, electronics, physics, medicine and others, and can be applied to a variety of technical fields such as analytical and immunological testing.

Description of Related Art

Currently, a number of marker molecules have been identified in breath that could be used to identify disease, disease progression, or to monitor therapeutic intervention and this list is expected increase dramatically since the analysis of breath is ideally suited for population-based studies in the developed and underdeveloped world.

The concept that blood, urine, and other body fluids and tissues can be collected and analyzed to yield information for diagnosis of disease states or to monitor disease progression and/or therapy is the foundation of modern medicine.

However, the use of breath as a collectable sample has not received comparable clinical use, as conducted studies have only been possible so far as a result of enhanced separation of gaseous molecules by gas chromatography, increased selectivity of mass or optical spectrometers and improved limits of detection from high parts-per-million to parts-per-billion.

Breath measurement has enormous potential, in part because of its inherent safety. The only requirement to collect a breath sample is that the subject must be breathing (spontaneously or mechanically supported). Breath analysis can be used to detect disease, monitor disease progression, or monitor therapy.

Recent advances in instrumentation may enable more of this potential to be realized. In particular, the wider availability of real-time, portable monitors would be a breakthrough.

It was discovered decades ago that atoms and molecules interacting with semiconductor surfaces influence surface properties of semiconductors, such as conductivity and surface potential. Seiyama (1962) and Taguchi (1970) first applied the discovery to gas detection by producing the first chemo-resistive, semiconductor gas sensors. Since then, semiconductor gas sensors have been widely used as domestic and industrial gas detectors for gas-leak alarms, process control, pollution control, etc.

Recent years have seen the introduction of solid-state sensors for the detection of different gases, which are based on metal oxide semiconductors. As with catalytic devices, which rely on the absorption of a gas on to a heated oxide surface, the absorption and/or subsequent reaction of a gas on the surface of the oxide produces an electrical conduction change in the metal-oxide itself on the account of the electronic processes involved in the reaction on its surface.

These conductivity changes relate to the amount of gas absorbed on the surface of the oxide and hence to its concentration in the surrounding atmosphere.

The metal-oxide semiconductor sensor is comprised of a tin oxide that is sintered on a small ceramic tube or surface. A coiled wire is placed through the center of the ceramic tube to act as the sensor's heater. Metal wires provide electrical contact between the tin oxide and the rest of the electronics.

The metal-oxide sensor requires between 300 mW and 600 mW of power to operate the sensor at elevated temperature between 300 and 450 degrees Celsius.

The combination of the sensor's operating temperature and composition of the metal-oxide yields different responses to various gases.

When a metal-oxide crystal, such as $ZnO_2$, is heated at a certain high temperature in the air, oxygen is adsorbed on the crystal surface with a negative charge. Then, the donor electrons in the crystal surface are transferred to the adsorbed oxygen, resulting in a removal of positive charges in a space charge layer. This surface potential is formed to serve as a potential barrier against electron flow.

Inside the sensor, electric current flows through the conjunction part (drain boundary) of $ZnO_2$ micro-crystals. At drain boundaries, adsorbed oxygen forms a potential barrier, which prevents carriers from moving freely.

The electrical resistance is attributed to this potential barrier. In the presence of a deoxidizing gas, the surface density of the negatively charged oxygen decreases, thus the barrier height in the drain boundary is reduced. The reduced barrier height decreases the sensor's resistance.

The relationship between the resistance of the sensor and the concentration of the deoxidizing gas can be expressed by the following equation over a certain range of gas concentration:

$$Rs=A*[C]*(-x) \quad \text{(Equation 1)}$$

Where Rs=electrical resistance of the sensor, A=constant, [C]=gas concentration, and (−x)=slope of the Rs curve. According to Equation 1, the relationship of the sensor's resistance to gas concentration is generally linear on a logarithmic scale within a practical range, determined by current market data and depending from the particular gas, to be from approximately a hundred ppm (parts per million) to several thousand ppm of gas concentration.

Modern metal-oxide methods and the method of preparing a sensitive surface with a laser may resemble the method disclosed herein. For example, a semiconductor oxide gas sensor was introduced through a research team led by Dr. S. Kawi from the department of chemical engineering of the National University of Singapore (NUS). However, researchers indicated that further and extensive experimentation was necessary to understand the nature of the involved processes and to explain the achieved results.

Another method to improve the quality and sensitivity of the $ZnO_2$ layer to tens of ppm is the method of using a laser to scan the sensor's surface. By using a laser, it is possible to change the density of the electrical charge on the sensor's sensitive layer.

The above-described methods and techniques have several disadvantages in common and cannot be used for investigations of gaseous mixtures with low concentration levels.

The use of Equation 1 can be limiting and becomes invalid for small concentrations of a gas because at low concentration levels, changes in the resistivity also occur under the influence of internal factors, such as diffusion and recombination, which are not taken into account by the formula.

The dependency on a logarithmic relationship derived from Equation 1 does not allow for selectively analyzing the effect of similar gaseous components on the semiconductor's sensing layer.

In the presence of destabilizing factors, such as a change in the temperature or a change in the flow of gas, the formula can no longer be applied. Consequently, the destabilizing factors are prevalent at small concentrations.

SUMMARY

Some of the advantages and objectives are as follows: (1) provide a method to detect, measure and monitor small concentrations of individual gases or gases in a gaseous mixture with high selectivity and high sensitivity; and (2) provide an instrument for various applications such as an accurate, non-invasive monitoring and diagnostic of pulmonary exclusions.

The technology described herein may be used for gas analysis such as in medicine, defense and military industries and food industries. In general, the technology can be used to determine quantitative and qualitative characteristics of components in a gaseous mixture with a high degree of selectivity and resolution.

Described herein are methods and devices for detection and quantitative and qualitative analysis of components in a gaseous mixture, distinguished by high selectivity and high resolution, and the technology allows one to discriminate the influence of individual gases, by themselves or in a mixture, on the microstructure of a sensor's sensitive layer. The device can use this influence to analyze and derive parameters related to gases, thus bypassing limitations imposed by traditional measuring and monitoring techniques. According to just one illustrative application, the device described herein provides effective alternatives in areas such as disease diagnostics and other areas and applications that previously have not been accessible or attainable with known practices.

In another aspect of the device, a model and a new process for determining the characteristics of various components within gaseous mixtures is disclosed. The device involves or includes sensitive and selective measurement of individual gases within mixtures.

According to another aspect, the methods disclosed are distinguished from other methods by high sensitivity and high selectivity and locates domains of dynamic stability and instability.

The methods are capable of determining boundaries of the domains of dynamic stability, where measurements can be extracted and domains of instability, where measurements cannot be predicted. Destabilizing factors, such as temperature or pressure fluctuations, which hinder measurements and deform the domains' boundaries, are taken into account.

Since the domains of stability and instability possess varying widths and can be regulated by changing certain parameters of the system, the techniques described herein reach desired domains for different applications.

According to the teachings herein, a class of algorithms can be used with the disclosed methods for the detection of individual components with very similar characteristics in gaseous mixtures through comparison of locations of individual domains of stability and instability, which are not identical within the measurement diapason.

Periodicity is introduced via one or more periodic variations of a physical attribute of the system into the initial parameters of Mathieu's equation. For example, introducing periodic variations includes introducing change through at least one of a valve or a pump of the system, varying over time a current flow associated with a sensor, and varying the physical surface profile of the sensor according to a regular pattern as viewed along the first direction and along a second direction.

These and other aspects and features of the invention will be more fully apparent from the following description and appended claims taken in conjunction with the accompanying figures.

DETAILED DESCRIPTION

Figure 1A:
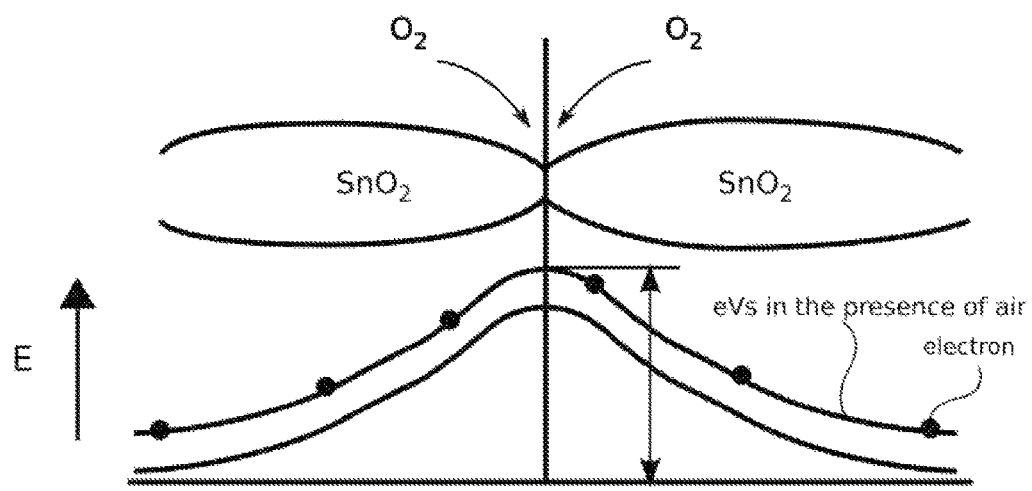
FIG. 1A shows a sensing mechanism in solid-state metal-oxide sensors according to one implementation of the invention without the presence of gas.
Figure 1B:
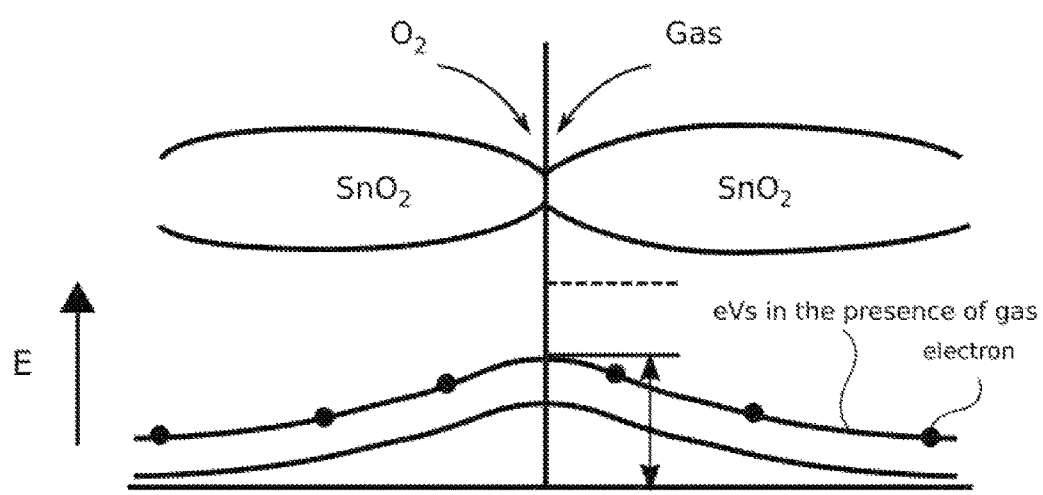
FIG. 1B shows the mechanism shown in FIG. 1A with the presence of gas.

By using a new methodology as described herein, it is possible to detect relatively low concentrations (e.g., tens ppm, hundreds ppb) of reducing gases and, with some applied limitations, and selectively distinguish certain gases from one another.

The functioning of sensors and calculation of their parameters may be observed during a state of dynamic equilibrium. In a steady state, any small variation or oscillation surrounding the predominant average value are deemed insignificant and are thrown out from the calculation. As a result, limitations occur and the sensor's output parameters are only predictable and calculated for a particular range of changing input parameters. For example, sensors work correctly within limited changing characteristics of the sensitive layer under gas influences. Due to the influence of internal factors in the body of the sensor, such as diffusion and recombination, discarding these small changes in relation to the predominant average value is incorrect and produces erroneous results.

Taking into account the periodic changes surrounding the predominant average value of the potential barrier, Equation 2 describes and allows analysis of processes in the sensitive layer of a sensor, and is free from the limitations described above.

$$\frac{\partial^2 q}{\partial t^2} - G*(Eo - Ex)*q = 0 \quad \text{(Equation 2)}$$

Where q is the charge, G is the conductance constant, Eo is the amplitude of the internal electric field, and Ex is the amplitude of the electric field at the boundary of the microcrystal which prevents carriers from moving freely.

Equation 2 can be simplified to an analysis of a second order differential equation in the following form:

$$\frac{\partial^2 q}{\partial t^2} + \lambda * p(t) * q = 0 \quad \text{(Equation 3)}$$

Where lambda, $\lambda$, is some constant, p(t) is a function of time which does not greatly vary with its average value. The function p(t), can be then rewritten as:

$$p(t) = \alpha*(1+\mu*f(t)) \quad \text{(Equation 4)}$$

where alpha, $\alpha$, and mu, $\mu$ are constants and $\mu < 1$ and f(t) is a periodic function of t with an angular frequency, omega, $\omega$, for which:

$$\int_0^\omega f(t)dt = 0 \quad \text{(Equation 5)}$$

If $\alpha*\lambda < 0$, then at a small enough $\mu$ there exists a place of instability.

For $\alpha*\lambda > 0$, Equation 3 can be written in the form below (Equation 6), which describes the range of stability and only in this range can solutions be predicted and calculated.

$$\frac{\partial^2 q}{\partial t^2} + \lambda^2 * (1 + \mu * f(t)) * q = 0 \quad \text{(Equation 6)}$$

The equation above can be solved using numerical approximation methods.

As a result, it is possible to determine domains of dynamic stability and instability separated by the occurrence of resonant oscillations, in which the amplitude is raised to detectable levels. (See FIG. 6.)

The following observations and conclusions can be made:

1. Under the influence of flow of gas on the reactive layer of a sensor, the value of the potential barrier does not change gradually with a change in concentration; instead there exist domains of dynamic stability, where parameters can be predicted and domains of dynamic instability, where parameters are unpredictable.

2. Only within domains of stability, it is possible to determine the influence of the external factors to the sensors' sensitive layer.

3. Since the domains of stability and instability possess varying widths, and can be regulated by changing certain parameters of the system, such as temperature, pressure, etc., the method provides a way to determine desired domains for different applications.

4. Measurement procedures within individual areas of dynamic stability can be established and also allow to travel between domains under control of certain parameters and conditions.

5. Comparing the domains of stability and instability for different gases produces the ability to perform selective analysis of the gases in the mixture.

6. The boundaries between zones of dynamic stability and instability can be found by scanning and detecting increasing amplitudes of oscillations in the diapason of the changing measurement parameters.

7. Detrimental factors simply deform the widths of domains of stability and instability without destroying them and are also taken into account in the method.

8. Each gas is described by a differential equation. A gaseous mixture may be described by a system of differential equations. The individual equations and the system of equations may be solved by conventional methods.

A device implementing the proposed method works as follows. An investigated gaseous mixture, for example the exhaled breath from a patient, is prepared and collected in a Gas Preparation Unit of the device, before processing. One purpose of the Gas Preparation Unit is to promote conditions such that the investigated gaseous mixtures at any time will be measured under reproducible or consistent conditions. The pressure, volume and temperature of the gaseous mixture can vary within the Gas Preparation Unit. Variations may be regulated with the aid of a microprocessor. Equilibrium, in many cases, is preferably achieved before processing of any gas sample.

A prepared gaseous mixture is then passed to a Measurement Assembly, which serves to determine the concentration of different components in the gaseous mixture. Internal conditions inside the Measurement Assembly, the control and regulation of various parameters, and influences on the process of passing the gases through the sensors, such as air quality, temperature of the sensing layer, speed at which the gaseous mixture is delivered to the sensing layer of the sensor, and the quality of the gaseous mixture itself, etc., are preferably regulated by one or more Control Units, which use the developed algorithm thus realizing the method. After measurement, the processed gaseous mixture is expelled from the Measurement Assembly, preparing the unit for a subsequent measurement.

The Measurement Assembly includes a predetermined number of sensors, which react with individual components of the gaseous mixture. The sensors' outputs, a series of analog signals, are then passed to a Data Acquisition Unit for amplification, filtration and digitization by an Analog-to-Digital Converter (ADC). Once digitized, the prepared data is transferred to a Data Consolidation Unit.

The Data Consolidation Unit serves to collect, store, and transfer information from each individual sensor to the microprocessor upon receiving a request. This allows for the consolidation and synchronization of individual subsystems, preventing the loss of data and increasing the dependability at the device. A data stream then leaves the Data Consolidation Unit directed for processing in the Control Unit. The Control Unit may be considered a large unit because it may be comprised of various subsystems. These subsystems are responsible for, for example, performing data conversion, providing internal communication between subsystems and producing necessary commands to accomplish device functionalities.

The DSP-based Data Processing Unit (DPU) functions to perform the actions of the Control Unit and houses the algorithm that controls the work of all subsystems in the device. The DPU also houses the algorithm to process the gathered data, thus realizing the proposed method. The DPU may communicate directly with the Control Unit and preferably shares data produced by the Data Consolidation Unit. The Control Unit performs, controls, and regulates the functionalities of the device. The functions of the Control Unit may include:

1. Receives processes, communicates and transfers data to the different units through a common interface. Achieved results are gathered and saved to a database and may be displayed in some form relatively soon after successful measurement and processing. The display may take the form of an indicator, light, flashing of a light, a digital result, text-based message, email notification, etc.

2. Controls actions performed by the electro-mechanical modules such as the pump, heater, piston, etc. The Control Unit receives and analyzes the signals from various mechanisms and performs the necessary actions and responses according to built-in application software.

3. Ensures synchronization of electronic blocks and subsystems.

The Control Unit is a multifunctional unit, which includes not only standard components, but also preferably contains an original Custom Logic Block. This block has original design circuitries for detecting areas of stability and instability in the changing parameters of the gaseous mixture as predicted by the described methods. Circuitries and their functionalities are described below. The Custom Logic Block is capable of managing data in 3D Space and in three or more dimensions when performing calculations or computations. Further, the Custom Logic Block is capable of treating a system of solutions for a plurality of unknown functions in addition to solving for an individual unknown function.

Independent modules, measurement tools and/or supplemental devices, when needed, are connected through the interface to the device. The device may include subassemblies and application software for calculating, locating and determining the boundaries of domains of stability and instability as described herein. Boundaries may be determined by analyzing some or all of the output data, which reflects changes in the parameters of the gaseous mixture. Furthermore, the subsystems used in the Control Unit insure reliability and dependability as well as provide ways to troubleshoot and diagnose the device in its entirety. The major units and their constraints are described below.

Figure 4:
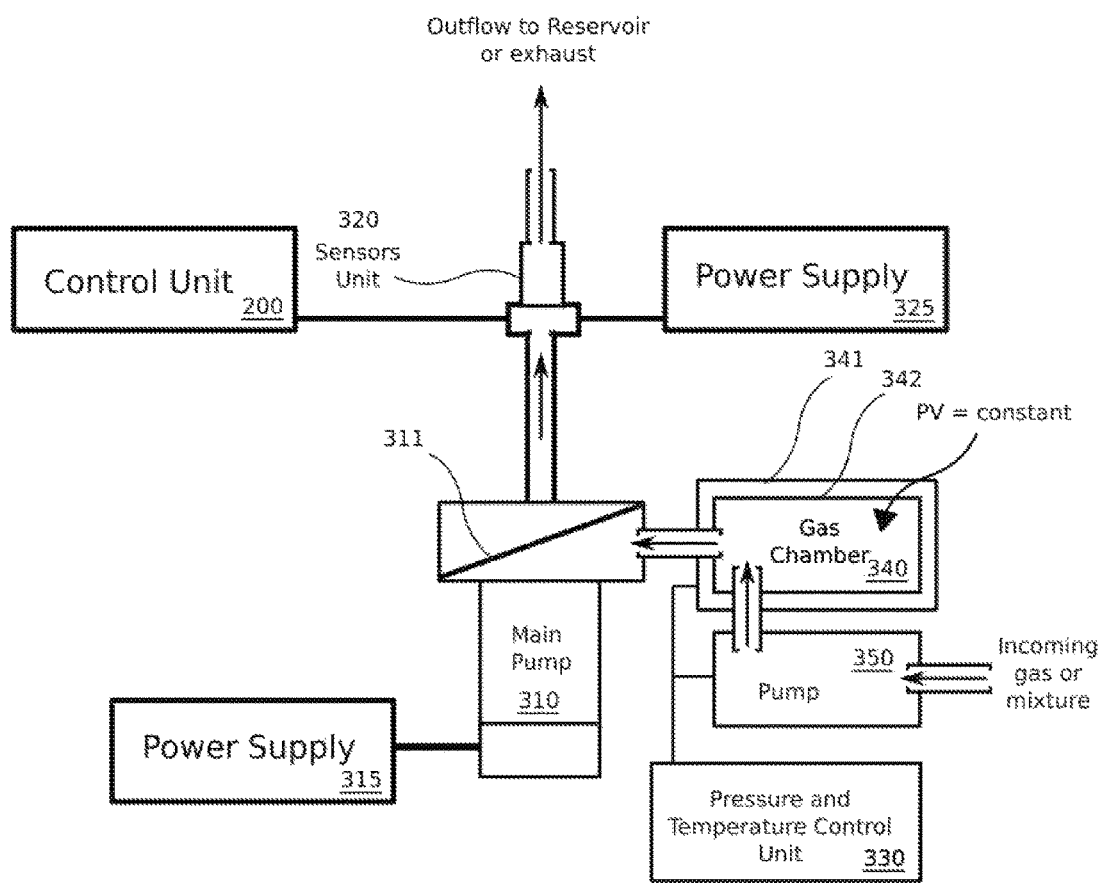
FIG. 4 shows a block diagram of a gas preparation unit according to one implementation of the invention

The Gas Preparation and Measurement Assembly Unit, 300, shown in FIG. 2, works in the following manner according to one implementation of the invention—with reference to FIG. 4 which shows the detailed structure of the Gas Preparation and Measurement Assembly with a sensor. A gaseous mixture, such as exhaled breath, is pumped with pump 2, 350, to the gas chamber, 340, as shown in FIG. 4.

The pressure and volume of the gaseous mixture in the gas chamber, 340, is regulated by, for example, a change in a position of a piston (not shown). The heating element, located in Pressure and Temperature Control subsystem, 330, built to work with the Gas chamber, 340, heats the mixture in the chamber to an assigned or designated temperature.

The gas chamber 340, is comprised of two cylinders, one, 342, inside the other, 341. The double walls and the inner cavity prevent or reduce the exchange of heat with the surroundings. A valve (not shown) prevents the gaseous mixture from leaving the gas chamber 340, allowing the mixture to reach equilibrium, i.e. PV (pressure and volume) =constant at an assigned temperature. Then, the valve is opened, allowing the mixture to move into the Sensors Unit, 320, for processing. The output signal of the Sensors Unit, 320, is then passed to the Control Unit, 200, while the gaseous mixture itself is exhausted to prepare the Sensor Unit, 320, for subsequent measurements.

Figure 5:
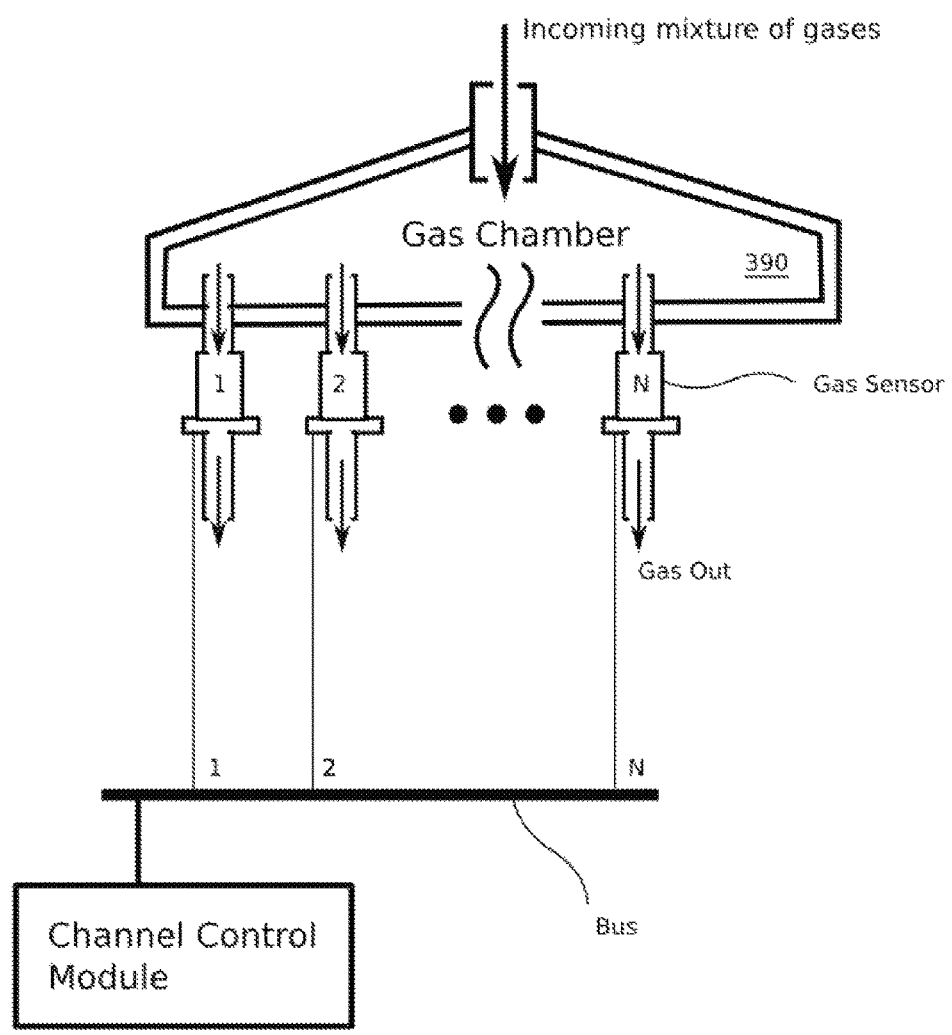
FIG. 5 shows a block diagram of a gas preparation unit assembly for a mixture of gases according to one implementation of the invention.

If a mixture of gases is being measured, then the Sensors Unit, 320, is modified according to the assembly of the Sensors Unit, 390, illustrated in FIG. 5. The Sensors Unit, 390, has a given number of sensors N (shown as 1, 2 . . . N), each of which is configured for the detection of a particular gas. The configuration for the detection of a specific gas requires the heating of the sensitive layer within a sensor to a temperature, which corresponds with the temperature at which the specific gas is most active. Each particular gas has its own optimal temperature. The heating of the sensing layer inside the sensor is achieved through the utilization of an internal, built-in heating element (not shown) in the sensor.

The speed with respect to time with which the gaseous mixture enters the Sensors Unit, 320, the time the gaseous mixture is in contact with the sensing layer of a sensor and other parameters are regulated, for example, by adjusting amount of gas and gas flow being delivered to the sensor housing. The gas which passes through or over the sensor, for example, sensor #1 of Sensor Unit 390 in FIG. 5, is collected in a reservoir (not shown). This gas can be utilized for further analysis, such as for determining the composition of the mixture or simply can be released back into the surroundings. The sensors' output signals—analog signals changing with respect to time—are detected and processed in the electronic subsystem(s) of the proposed device. Refer to FIGS. 2-5.

The electronic subsystems work in the following manner according to one implementation of the invention. The outputs of the sensors, in form of analog signals, are transferred to the inputs of a Data Acquisition Unit, 100 in FIG. 2. In the Data Acquisition Unit, signals are amplified, filtered, and converted to a digital form. An Analog-to-Digital Converter, 110, is used. Then the processed signal enters the Data Consolidation Unit, 500, where FIFOs and other storage elements are used to save and synchronize the data streams produced inside the internal subsystems. This ensures the functionality and reliability of the processor, the Control Unit, 200, and the entire device. FIG. 3 shows the structure of the Control Unit, which is responsible for controlling the major processes and functionalities of different components and the device itself, including power distribution, security, mechanical arms control, valve operations, piston movement, etc. The Control Unit also treats and prepares information to be transferred between the internal units.

Figure 6:
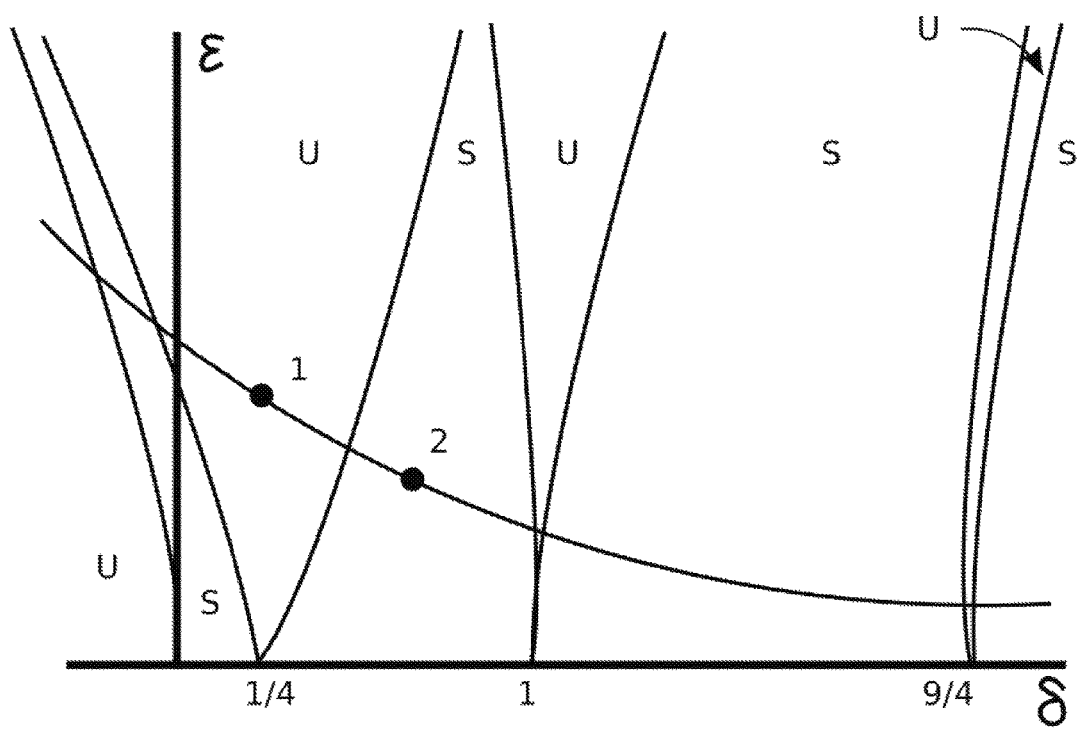
FIG. 6 shows transition curves in Mathieu's equations demonstrating areas of stability and instability according to one implementation of the invention.

Original Custom Logic, 222, implemented in the Control Unit, is involved in the detection of the boundaries of stability and instability—such as the boundaries, which separate stable and unstable regions, shown in FIG. 6. With reference to FIG. 3, the indicated subsystem includes an asynchronous block, 227, that operates the application software to determine the domains of stability and instability through the analysis of the changes in the output parameters of the gaseous mixture as outlined by the methods described herein. The Control Unit subsystem also includes time-dependent logic components (not shown), switching capacitors and other elements used to determine and analyze the characteristics of oscillation occurring at the boundaries of domains of stability and instability.

Figure 2:
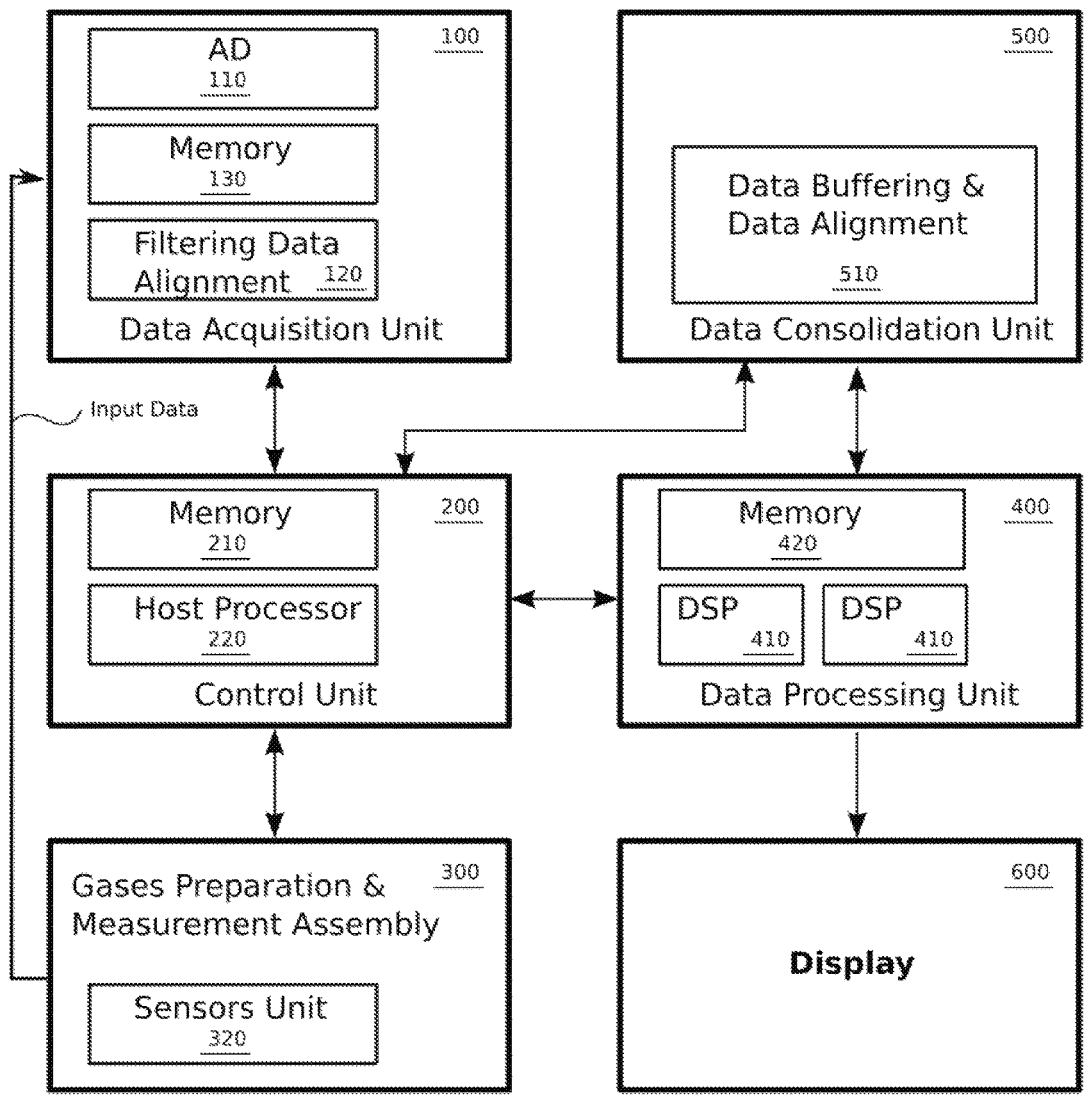
FIG. 2 shows a block diagram of a device for measuring and analyzing exhaled gases based on one implementation of one of the methods disclosed herein.
Figure 3:
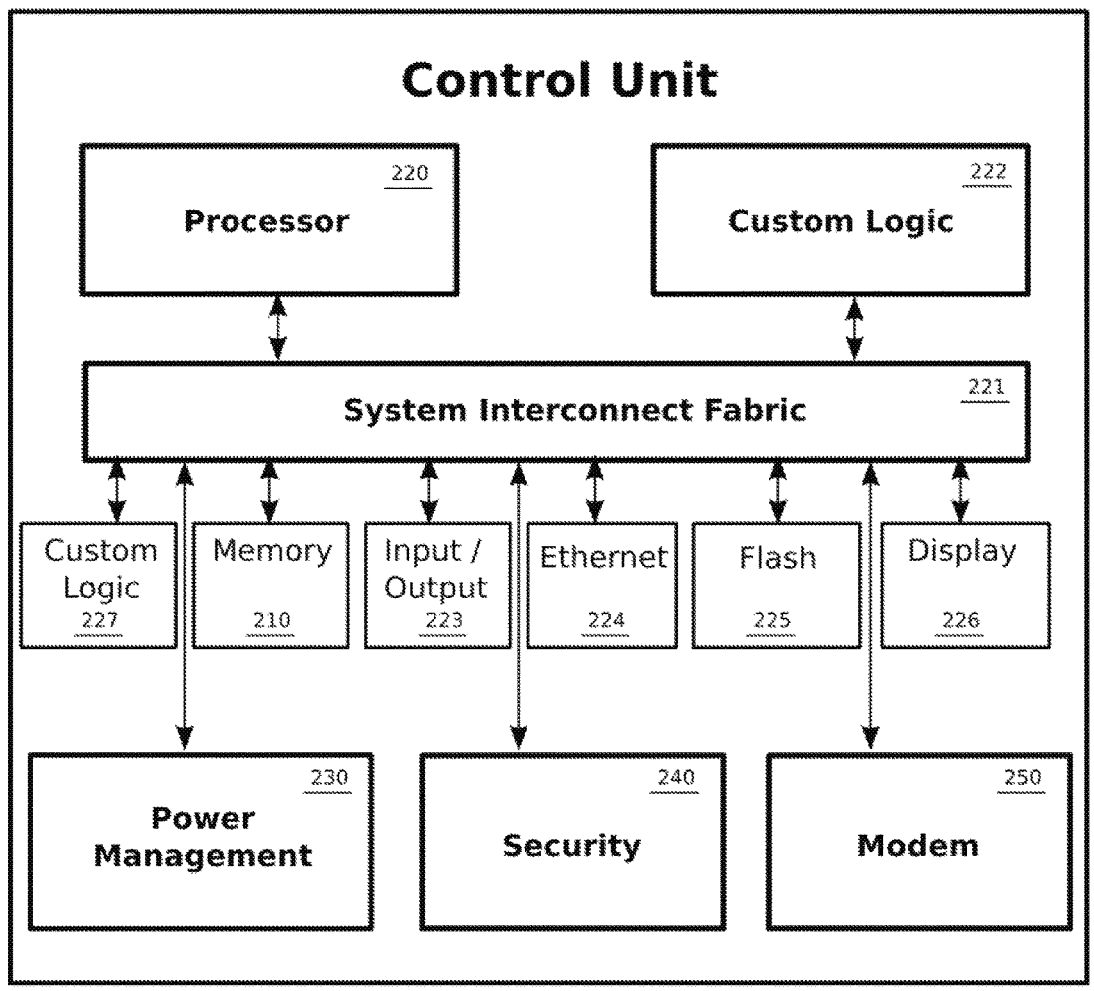
FIG. 3 shows a block diagram of a control unit, which includes a custom logic block according to one implementation of the invention. There are subassemblies conforming to an original algorithm to process the gathered information and perform functionalities of a device involving methods described herein.

The Data Processing Unit, 400, shown in FIG. 2 includes an implemented algorithm that realizes one embodiment of a proposed method as well as algorithms that utilize proper operations of the device and appropriate software applications to insure continuity, reliability and dependability of the individual subsystems and their interaction within the device. Furthermore, the algorithms define and control the data stream(s) within the device, transferring the data through the interface. Standard protocols such as universal asynchronous receiver/transmitter UART (serial), 226, Ethernet (TCP/IP), 224, Flash, 225, and others can be implemented to aid and utilize the information exchange.

Sampling, sensing and calculation of values related to a concentration of a gas may be repeated so as to perform uninterrupted monitoring of a gas. Such repeating may be done as frequently as possible for continuous monitoring, or may be done at predefined intervals so as to provide intermittent updates of values related to a gas concentration or intermittent monitoring of a gas. Time may be utilized as a parameter in processing to assist in determining if or when the system is in the stable or unstable domain at the general instant of when the measurement occurs.

Simultaneous measurement of various gases in a gaseous mixture can be made utilizing the methods described herein by distributing incoming gas into different channels each equipped with its own sensor for the targeted gas and then using the methods described herein to calculate the concentration of each gas in its respective channel. For example, one channel could measure a concentration of nitrogen, and a second channel could measure a concentration of oxygen.

In one implementation, ambient air is pumped into the system to clear the sensor area of measured gases and prepare the sensing layer of the sensor for subsequent measurements, reducing the time between measurements. The methods described herein allow monitoring the state of the system in real time, when a measurement is being performed. In another implementation, the methods described herein do not require prior preparation or calibration of the sensors or system in order to take a measurement.

Periodicity. Above in Equation 4 and Equation 6, f(t) is a periodic function of time t. In the system and methods described herein, a physical parameter may be periodically changed with respect to time to set up the initial parameters of the equation or equations to solve. Periodicity as used herein refers to a repeating pattern with respect to time. The following are three examples of implementing periodicity into the system.

Gas flow. According to one implementation, a sample is continuously delivered to the sensor for measurement by the sensor in a straight forward, uniform manner. For example, the sample is held at a first constant pressure when released to the sensor. Periodicity can be introduced by varying the gas flow to the sensor in a uniform, repeated pattern. That is, the speed of the gas flow is regulated such that for two seconds the gas flows to the sensor, then stops, then flows for the same amount of time, then stops. Alternatively, as another example, the gas flow is slowed instead of stopped by reducing an opening of a valve separating the sample from the sensor, or by varying the pressure of the gaseous sample by pressurizing the gaseous sample to one of various predetermined pressures at certain times during a measuring or sampling period. A pattern repeats or cycles until all measurement data is collected from the sensor. Alternatively, gas flow is provided at one speed (e.g., volume or mass per unit time) for a certain time, then increased or decreased to another speed for a same or different time, and then returned to the original speed. Setting a repeating pattern by manipulating the flow of the sample onto or through the sensor for measurement is one way to implement periodicity for the initial condition of Mathieu's equation.

Electric current. Alternatively, periodicity may be implemented by varying a physical condition related to the electric current associated with the device or system. For example, periodicity may be introduced by varying the supplied voltage to the output of the sensor. In contrast to published data sheets from commercial sensor vendors which indicate a constant voltage supply to a sensor's output leads, to implement periodicity in the instant system, an initial voltage can be varied according to a pre-set repeated pattern. According to a first implementation, a first pre-determined constant voltage between three and five volts is supplied over an initial time interval. At the end of the initial time interval (e.g., 10 seconds, 15 seconds), the voltage is modified to another pre-determined voltage for another time interval. This procedure is repeated for a predetermined period such as two minutes. Successive two minute intervals may repeat the changes according to the first two minute interval. While the implementation has been described with respect to seconds, the time interval may be reduced to milliseconds, micro-seconds and so forth to a desired level of periodicity. The numbers above are merely used to provide an illustration. Accordingly, the applied voltage to the output of the sensor is the parameter that is used to provide the condition of periodicity to the system. Alternatively, a varying resistance or varying amount of current flowing in the system can be utilized to introduce the periodicity to the system and calculations associated therewith.

Surface geometry. Yet another way to implement a repeatable pattern in the system for measuring concentration of a gas is to physically change the topology of the sensing layer of the sensor. According to presently available commercial sensors, each sensor has a continuous, uniform and rectangular sensing surface area with which gas molecules interact or chemically react to produce an electrical output. According to a first theoretical understanding of the measuring mechanism, the sensing layer at rest produces a particular output. Upon flow of a gas sample over the sensing layer, gas molecules chemically react with the surface of the sensor. The electrical output changes as a result of the chemical reaction between molecules of the sensing layer and molecules of the gas or gaseous mixture. (Or electrical output changes as a result of the number of gas molecules absorbed by the sensing layer).

One factor that affects this chemical interaction and ultimately the output of the sensor, which is then used to calculate the concentration by employing Mathieu's equation or variation thereof, is the distance between the gas molecules and molecules of the sensing layer. According to a first implementation, the sensing layer is uniform, i.e. one flat, level surface. The density (number of the absorbed molecules divided by area) is constant. The length of the reacting surface area is constant. According to a second implementation of the system, a sensing layer is formed such that the flux of gas molecules react with different areas of the sensing layer and the sensing surface is not constant but rather the topology of the sensing layer changes in a pre-formed, repeatable manner. A simple design for the sensing layer is a square wave, or a step-up step-down function that repeats in one or two dimensions. This can be done with one material or combining several materials for the purpose of achieving and introducing this change of one level, then a higher or lower level, then return to the original level, and then repeating the sequence for the length of the sensing layer. Effectively, the resistance of the sensing layer is periodically varied, which is one of the initial parameters utilized in Mathieu's equation. If resistance is not constant but rather is varied with respect to time in a repeatable, periodic fashion then such physical or geographic variation of the sensor surface acts to provide periodicity.

Conclusion. Although the present invention has been described with reference to specific exemplary embodiments, it will be evident that modifications and changes can be made to these embodiments without departing from the broader spirit of the invention. Accordingly, the specification and drawings are to be regarded in an illustrative sense rather than in a restrictive sense.

Similarly, while certain exemplary embodiments have been described and shown in the accompanying drawings, it is to be understood that such embodiments are merely illustrative and not restrictive of the broad invention and that this invention is not limited to the specific constructions and arrangements shown and described therein, since various other modifications may be made according to the abilities of those ordinarily skilled in the art upon studying this disclosure. The disclosed embodiments may be readily modifiable as facilitated by enabling technological advancements without departing from the principals of the present disclosure.

We claim:

1. A device for detecting a concentration of a component of a gaseous sample, the device comprising:
   a trapping chamber for temporarily containing a volume of the sample;
   a sensing chamber proximate to the trapping chamber and capable of being coupled with the trapping chamber so as to receive a portion of the sample from the trapping chamber during operation of the device;
   a valve separating the sensing chamber from the trapping chamber;
   a pump coupled with the trapping chamber, and wherein the pump is configured to pressurize the gaseous sample in the trapping chamber;
   a control unit in communication with the valve so as to control via operation of the valve introduction of gaseous sample into the sensing chamber, and wherein the control unit is in communication with the pump so as to control a pressure of the gaseous sample, and wherein the control unit is programmed with instructions to introduce periodicity by introducing changes through at least one of the valve and the pump;
   a power supply to provide electrical current to components of the device; a sensor in electronic communication with the power supply, and wherein the sensor includes a sensing surface, and wherein the sensor surface is exposed to the inside of the sensing chamber, and wherein the sensor is in electronic communication with the power supply; and
   a memory in electronic communication with the power supply, and wherein the memory is configured with instructions that cause the device to:
      make a computation related to Mathieu's Equation with a value for each initial condition of such equation to determine when a value associated with an electrical change in the sensor is in a stable domain, wherein a stable domain is a numeric domain where values can be predicted in accordance with the said Mathieu's Equation, and wherein an unstable domain is a numeric domain where a resulting value is unreliable; and
      when the value associated with the electrical change is in a stable domain, determine a numerical value associated with the concentration of the component in the sample based on an electrical characteristic of the sensor.

2. The device of claim 1, and wherein the sensing chamber is of a fixed volume.

3. The device of claim 1, and wherein the trapping chamber is of a fixed volume.

4. The device of claim 1, wherein Mathieu's Equation is of a form:

$$\frac{\partial^2 x}{\partial t^2} + \lambda^2 \cdot (1 + \mu \cdot f(t)) \cdot x = 0$$

where lambda, $\lambda$, represents a numeric constant, where mu, $\mu$, represents another numeric constant, and where t represents time.

5. A device for detecting a concentration of a component of a gaseous sample, the device comprising:
   a trapping chamber for temporarily containing a volume of the sample;
   a sensing chamber proximate to and coupled with the trapping chamber;
   a pump coupled with the trapping chamber and sensing chamber, and wherein the pump is configured to pressurize the gaseous sample in the trapping chamber;
   a control unit in communication with the pump so as to control a pressure of the gaseous sample;
   a sensor unit, the sensor unit including a sensor, and wherein the sensor includes a sensing surface, and wherein the sensor surface is exposed to the inside of the sensing chamber;
   a power supply in electronic communication with the control unit and the sensor unit; and
   a memory configured with instructions that cause the device to:
      provide a periodic change to a condition of the sensor;
      make a computation related to Mathieu's Equation to determine when a value associated with an electrical change in the sensor is in a stable domain, wherein a stable domain is a numeric domain where values can be predicted in accordance with the said Mathieu's Equation, and wherein an unstable domain is a numeric domain where a resulting value is unreliable; and when the value associated with the electrical change is in a stable domain, determine a numerical value associated with the concentration of the component in the sample based on the said periodically changed condition of the sensor.

6. The device of claim 5, and wherein the periodic change to the condition of the sensor includes varying over time a supplied voltage to the output of the sensor.

7. The device of claim 6, and wherein the varying includes providing a first constant voltage to the sensor at a value approximately between three and five volts over a first time interval and providing a second constant voltage to the sensor at a second value over a second time interval.

8. The device of claim 7, and wherein the first time interval is substantially the same in magnitude as the second time interval.

9. The device of claim 6, and wherein the varying includes providing a voltage according to a sinusoidal function.

10. The device of claim 5, wherein the condition of the sensor is a temperature of the sensing layer of the sensor.

11. The device of claim 5, wherein the condition of the sensor is electronic resistance associated with the sensor, i.e. the inability of a current or a flow of charged particles to move through the sensing layer to the sensor output, and wherein variation of the initial resistance, when no gas present, facilitates determination of an initial condition of Mathieu's Equation.

12. A method for determining a concentration of a component of a gaseous sample, the method comprising:
[1] trapping a volume of the gaseous sample in a chamber;
[2] exposing the gaseous sample in the chamber to a sensor when the sensor is powered by a power supply;
[3] providing a periodic variation to a physical characteristic of the sensor or the system;
[4] detecting a change in electric current associated with the sensor as a result of interaction of the sample with the sensor;
[5] capturing a copy of the value associated with the change in current;
[6] performing computer instructions related to Mathieu's Equation with a value for each initial condition of Mathieu's Equation by determining when a value associated with the detected current is in a stable domain, wherein the values associated with the initial conditions are related to conditions of the sample in the chamber; and
[7] when the value associated with the detected current is in a stable domain, determining the concentration of the component of the sample using the captured copy of the value associated with the change in current.

13. The method of claim 12, wherein providing the periodic variation to the physical characteristic of the sensor includes varying over time a supplied voltage to the output of the sensor, and wherein variation of the supplied voltage facilitates designating an initial condition to be applied for performing analysis using Mathieu's Equation.

14. The method of claim 13, and wherein the varying over time the supplied voltage includes providing the supplied voltage according to a step function.

15. The method of claim 12, and wherein providing the periodic variation to the physical characteristic of the sensor includes varying over time the current flow associated with the sensor.

16. The method of claim 12, and wherein providing the periodic variation to the physical characteristic of the sensor includes varying the physical surface profile of the sensor according to a regular pattern as viewed along a first direction.

17. The method of claim 12, and wherein providing the periodic variation to the physical characteristic of the sensor includes varying the surface profile of the sensor according to a regular pattern as viewed along a first direction and a second direction.

18. The method of claim 12, and wherein providing the periodic variation to the physical characteristic of the sensor includes varying a temperature of the sensing layer of the sensor.

* * * * *